US008641698B2

(12) United States Patent
Sanchez et al.

(10) Patent No.: US 8,641,698 B2
(45) Date of Patent: Feb. 4, 2014

(54) PIVOT POINT ARM FOR ROBOTIC SYSTEM USED TO PERFORM A SURGICAL PROCEDURE

(75) Inventors: Dan Sanchez, Santa Barbara, CA (US); Michael Black, Palo Alto, CA (US); Scott Hammond, Mill Valley, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 858 days.

(21) Appl. No.: 11/357,392

(22) Filed: Feb. 17, 2006

(65) Prior Publication Data

US 2006/0259019 A1   Nov. 16, 2006

Related U.S. Application Data

(60) Continuation of application No. 10/411,651, filed on Apr. 10, 2003, now abandoned, which is a division of application No. 09/847,736, filed on May 1, 2001, now abandoned.

(51) Int. Cl.
*A61B 1/01* (2006.01)

(52) U.S. Cl.
USPC ............................................................ 606/1

(58) Field of Classification Search
USPC .......................... 606/1, 32, 41; 128/849–852
See application file for complete search history.

(56) References Cited

U.S. PATENT DOCUMENTS

| 977,825 A | 12/1910 | Murphy |
| 3,171,549 A | 3/1965 | Orloff |
| 3,280,991 A | 10/1966 | Melton et al. |
| 4,058,001 A | 11/1977 | Waxman |
| 4,128,880 A | 12/1978 | Cray, Jr. |
| 4,221,997 A | 9/1980 | Flemming |
| 4,367,998 A | 1/1983 | Causer |
| 4,401,852 A | 8/1983 | Noso et al. |
| 4,456,961 A | 6/1984 | Price et al. |
| 4,460,302 A | 7/1984 | Moreau et al. |
| 4,474,174 A | 10/1984 | Petruzzi |
| 4,491,135 A | 1/1985 | Klein |
| 4,503,854 A | 3/1985 | Jako |
| 4,517,963 A | 5/1985 | Michel |
| 4,523,884 A | 6/1985 | Clement et al. |
| 4,586,398 A | 5/1986 | Yindra |

(Continued)

FOREIGN PATENT DOCUMENTS

| DE | 9204118.3 U1 | 7/1992 |
| DE | 4310842 C2 | 1/1995 |

(Continued)

OTHER PUBLICATIONS

Abstract of a presentation "3-D Vision Technology Applied to Advanced Minimally Invasive Surgery Systems" given at the 3rd World Congress of Endoscopic Surgery in Bordeaux, Jun. 18-20, 1992 (1 page total).

(Continued)

*Primary Examiner* — Aaron Roane

(57) ABSTRACT

A pivot port that can provide a pivot point for a surgical instrument. The pivot port may be held in a stationary position by a support arm assembly that is attached to a table. The pivot port may include either an adapter or a ball joint that can support the surgical instrument. The pivot port allows the instrument to pivot relative to a patient.

7 Claims, 1 Drawing Sheet

(56) References Cited

U.S. PATENT DOCUMENTS

| | | | |
|---|---|---|---|
| 4,604,016 A | 8/1986 | Joyce | |
| 4,616,637 A | 10/1986 | Caspari et al. | |
| 4,624,011 A | 11/1986 | Watanabe et al. | |
| 4,633,389 A | 12/1986 | Tanaka et al. | |
| 4,635,292 A | 1/1987 | Mori et al. | |
| 4,635,479 A | 1/1987 | Salisbury, Jr. et al. | |
| 4,638,799 A | 1/1987 | Moore | |
| 4,641,292 A | 2/1987 | Tunnel et al. | |
| 4,655,257 A | 4/1987 | Iwashita | |
| 4,672,963 A | 6/1987 | Barken | |
| 4,676,243 A | 6/1987 | Clayman | |
| 4,728,974 A | 3/1988 | Nio et al. | |
| 4,762,455 A | 8/1988 | Coughlan et al. | |
| 4,791,934 A | 12/1988 | Brunnett | |
| 4,791,940 A | 12/1988 | Hirschfeld et al. | |
| 4,794,912 A | 1/1989 | Lia | |
| 4,815,006 A | 3/1989 | Andersson et al. | |
| 4,815,450 A | 3/1989 | Patel | |
| 4,837,734 A | 6/1989 | Ichikawa et al. | |
| 4,852,083 A | 7/1989 | Niehaus et al. | |
| 4,853,874 A | 8/1989 | Iwamoto et al. | |
| 4,854,301 A | 8/1989 | Nakajima | |
| 4,860,215 A | 8/1989 | Seraji | |
| 4,863,133 A | 9/1989 | Bonnell | |
| 4,883,400 A | 11/1989 | Kuban et al. | |
| 4,930,494 A | 6/1990 | Takehana et al. | |
| 4,945,479 A | 7/1990 | Rusterholz et al. | |
| 4,949,717 A | 8/1990 | Shaw | |
| 4,954,952 A | 9/1990 | Ubhayakar et al. | |
| 4,965,417 A | 10/1990 | Massie | |
| 4,969,709 A | 11/1990 | Sogawa et al. | |
| 4,969,890 A | 11/1990 | Sugita et al. | |
| 4,979,933 A | 12/1990 | Runge | |
| 4,979,949 A | 12/1990 | Matsen, III et al. | |
| 4,980,626 A | 12/1990 | Hess et al. | |
| 4,989,253 A | 1/1991 | Liang et al. | |
| 4,996,975 A | 3/1991 | Nakamura | |
| 5,019,968 A | 5/1991 | Wang et al. | |
| 5,020,001 A | 5/1991 | Yamamoto et al. | |
| 5,046,375 A | 9/1991 | Salisbury, Jr. et al. | |
| 5,065,741 A | 11/1991 | Uchiyama et al. | |
| 5,078,140 A | 1/1992 | Kwoh | |
| 5,086,401 A | 2/1992 | Glassman et al. | |
| 5,091,656 A | 2/1992 | Gahn | |
| 5,097,829 A | 3/1992 | Quisenberry | |
| 5,097,839 A | 3/1992 | Allen | |
| 5,098,426 A | 3/1992 | Sklar et al. | |
| 5,105,367 A | 4/1992 | Tsuchihashi et al. | |
| 5,109,499 A | 4/1992 | Inagami et al. | |
| 5,123,095 A | 6/1992 | Papadopoulos et al. | |
| 5,131,105 A | 7/1992 | Harrawood et al. | |
| 5,142,930 A | 9/1992 | Allen et al. | |
| 5,145,227 A | 9/1992 | Monford, Jr. | |
| 5,166,513 A | 11/1992 | Keenan et al. | |
| 5,175,694 A | 12/1992 | Amato | |
| 5,182,641 A | 1/1993 | Diner et al. | |
| 5,184,601 A | 2/1993 | Putman | |
| 5,187,574 A | 2/1993 | Kosemura et al. | |
| 5,196,688 A | 3/1993 | Hesse et al. | |
| 5,201,325 A | 4/1993 | McEwen et al. | |
| 5,201,743 A | 4/1993 | Haber et al. | |
| 5,217,003 A | 6/1993 | Wilk | |
| 5,221,283 A | 6/1993 | Chang | |
| 5,228,429 A | 7/1993 | Hatano | |
| 5,230,623 A | 7/1993 | Guthrie et al. | |
| 5,236,432 A | 8/1993 | Matsen, III et al. | |
| 5,251,127 A | 10/1993 | Raab | |
| 5,257,999 A | 11/1993 | Slanetz, Jr. | |
| 5,271,384 A | 12/1993 | McEwen et al. | |
| 5,279,309 A * | 1/1994 | Taylor et al. | 600/595 |
| 5,282,806 A | 2/1994 | Haber | |
| 5,289,273 A | 2/1994 | Lang | |
| 5,289,365 A | 2/1994 | Caldwell et al. | |
| 5,299,288 A | 3/1994 | Glassman et al. | |
| 5,300,926 A | 4/1994 | Stoeckl | |
| 5,303,148 A | 4/1994 | Mattson et al. | |
| 5,304,185 A | 4/1994 | Taylor | |
| 5,305,203 A | 4/1994 | Raab | |
| 5,305,427 A | 4/1994 | Nagata | |
| 5,309,717 A | 5/1994 | Minch | |
| 5,313,306 A | 5/1994 | Kuban et al. | |
| 5,320,630 A | 6/1994 | Ahmed | |
| 5,337,732 A | 8/1994 | Grundfest et al. | |
| 5,339,799 A | 8/1994 | Kami et al. | |
| 5,343,385 A | 8/1994 | Joskowicz et al. | |
| 5,343,391 A | 8/1994 | Mushabac | |
| 5,345,538 A | 9/1994 | Narayannan et al. | |
| 5,357,962 A | 10/1994 | Green | |
| 5,368,015 A | 11/1994 | Wilk | |
| 5,368,428 A | 11/1994 | Hussey et al. | |
| 5,371,536 A | 12/1994 | Yamaguchi | |
| 5,375,588 A | 12/1994 | Yoon | |
| 5,382,885 A | 1/1995 | Salcudean et al. | |
| 5,388,987 A | 2/1995 | Badoz et al. | |
| 5,395,369 A | 3/1995 | McBrayer et al. | |
| 5,397,323 A | 3/1995 | Taylor et al. | |
| 5,402,801 A | 4/1995 | Taylor | |
| 5,403,319 A | 4/1995 | Matsen, III et al. | |
| 5,408,409 A | 4/1995 | Glassman et al. | |
| 5,410,638 A | 4/1995 | Colgate et al. | |
| 5,417,210 A | 5/1995 | Funda et al. | |
| 5,417,701 A | 5/1995 | Holmes | |
| 5,422,521 A | 6/1995 | Neer et al. | |
| 5,431,645 A | 7/1995 | Smith et al. | |
| 5,434,457 A | 7/1995 | Josephs et al. | |
| 5,441,042 A | 8/1995 | Putman | |
| 5,442,728 A | 8/1995 | Kaufman et al. | |
| 5,443,484 A | 8/1995 | Kirsch et al. | |
| 5,445,166 A | 8/1995 | Taylor | |
| 5,451,924 A | 9/1995 | Massimino et al. | |
| 5,455,766 A | 10/1995 | Schaller et al. | |
| 5,458,547 A | 10/1995 | Teraoka et al. | |
| 5,458,574 A | 10/1995 | Machold et al. | |
| 5,476,010 A | 12/1995 | Fleming et al. | |
| 5,490,117 A | 2/1996 | Oda et al. | |
| 5,490,843 A | 2/1996 | Hildwein et al. | |
| 5,494,034 A | 2/1996 | Schlondorff et al. | |
| 5,506,912 A | 4/1996 | Nagasaki et al. | |
| 5,512,919 A | 4/1996 | Araki | |
| 5,515,478 A | 5/1996 | Wang | |
| 5,544,654 A | 8/1996 | Murphy et al. | |
| 5,553,198 A | 9/1996 | Wang et al. | |
| 5,562,503 A | 10/1996 | Ellman et al. | |
| 5,571,072 A | 11/1996 | Kronner | |
| 5,571,110 A | 11/1996 | Matsen, III et al. | |
| 5,572,999 A | 11/1996 | Funda et al. | |
| 5,609,560 A | 3/1997 | Ichikawa et al. | |
| 5,626,595 A | 5/1997 | Sklar et al. | |
| 5,629,594 A | 5/1997 | Jacobus et al. | |
| 5,630,431 A | 5/1997 | Taylor | |
| 5,631,973 A | 5/1997 | Green | |
| 5,636,259 A | 6/1997 | Khutoryansky et al. | |
| 5,649,956 A | 7/1997 | Jensen et al. | |
| 5,657,429 A | 8/1997 | Wang et al. | |
| 5,658,250 A | 8/1997 | Blomquist et al. | |
| 5,676,673 A | 10/1997 | Ferre et al. | |
| 5,695,500 A | 12/1997 | Taylor et al. | |
| 5,696,574 A | 12/1997 | Schwaegerle | |
| 5,696,837 A | 12/1997 | Green | |
| 5,718,038 A | 2/1998 | Takiar et al. | |
| 5,727,569 A | 3/1998 | Benetti et al. | |
| 5,735,290 A | 4/1998 | Sterman et al. | |
| 5,737,711 A | 4/1998 | Abe | |
| 5,749,362 A | 5/1998 | Funda et al. | |
| 5,754,741 A * | 5/1998 | Wang et al. | 700/251 |
| 5,762,458 A | 6/1998 | Wang et al. | |
| 5,766,126 A | 6/1998 | Anderson | |
| 5,776,126 A | 7/1998 | Wilk et al. | |
| 5,779,623 A | 7/1998 | Bonnell | |
| 5,792,135 A | 8/1998 | Madhani et al. | |
| 5,792,178 A | 8/1998 | Welch et al. | |
| 5,797,900 A | 8/1998 | Madhani et al. | |
| 5,800,423 A | 9/1998 | Jensen | |
| 5,807,284 A | 9/1998 | Foxlin | |

(56) References Cited

U.S. PATENT DOCUMENTS

| | | | |
|---|---|---|---|
| 5,807,377 A | 9/1998 | Madhani et al. | |
| 5,807,378 A | 9/1998 | Jensen et al. | |
| 5,808,665 A | 9/1998 | Green | |
| 5,810,712 A * | 9/1998 | Dunn | 600/114 |
| 5,810,880 A | 9/1998 | Jensen et al. | |
| 5,813,813 A | 9/1998 | Daum et al. | |
| 5,814,038 A | 9/1998 | Jensen et al. | |
| 5,817,084 A | 10/1998 | Jensen | |
| 5,825,982 A | 10/1998 | Wright et al. | |
| 5,827,319 A | 10/1998 | Carlson et al. | |
| 5,836,869 A | 11/1998 | Kudo et al. | |
| 5,844,824 A | 12/1998 | Newman et al. | |
| 5,855,583 A | 1/1999 | Wang et al. | |
| 5,859,934 A | 1/1999 | Green | |
| 5,860,995 A | 1/1999 | Berkelaar | |
| 5,876,325 A * | 3/1999 | Mizuno et al. | 600/102 |
| 5,878,193 A | 3/1999 | Wang et al. | |
| 5,882,206 A | 3/1999 | Gillio | |
| 5,887,121 A | 3/1999 | Funda et al. | |
| 5,898,599 A | 4/1999 | Massie et al. | |
| 5,904,702 A | 5/1999 | Ek et al. | |
| 5,906,630 A | 5/1999 | Anderhub et al. | |
| 5,907,664 A | 5/1999 | Wang et al. | |
| 5,911,036 A | 6/1999 | Wright et al. | |
| 5,920,395 A | 7/1999 | Schultz | |
| 5,931,832 A | 8/1999 | Jensen | |
| 5,950,629 A | 9/1999 | Taylor et al. | |
| 5,951,475 A | 9/1999 | Gueziec et al. | |
| 5,951,587 A | 9/1999 | Qureshi et al. | |
| 5,954,731 A | 9/1999 | Yoon | |
| 5,957,902 A | 9/1999 | Teves | |
| 5,980,782 A | 11/1999 | Hershkowitz et al. | |
| 5,984,932 A | 11/1999 | Yoon | |
| 6,006,127 A | 12/1999 | Van Der Brug et al. | |
| 6,024,695 A | 2/2000 | Taylor et al. | |
| 6,079,681 A | 6/2000 | Stern et al. | |
| 6,080,181 A | 6/2000 | Jensen et al. | |
| 6,106,511 A | 8/2000 | Jensen | |
| 6,110,182 A * | 8/2000 | Mowlai-Ashtiani | 606/130 |
| 6,120,433 A | 9/2000 | Mizuno et al. | |
| 6,201,984 B1 | 3/2001 | Funda et al. | |
| 6,206,903 B1 | 3/2001 | Ramans | |
| 6,223,100 B1 | 4/2001 | Green | |
| 6,226,566 B1 | 5/2001 | Funda et al. | |
| 6,231,526 B1 | 5/2001 | Taylor et al. | |
| 6,246,200 B1 | 6/2001 | Blumenkranz et al. | |
| 6,259,806 B1 | 7/2001 | Green et al. | |
| 6,306,146 B1 * | 10/2001 | Dinkler | 606/130 |
| 6,309,397 B1 | 10/2001 | Julian et al. | |
| 6,312,435 B1 | 11/2001 | Wallace et al. | |
| 6,331,181 B1 | 12/2001 | Tierney et al. | |
| 6,346,072 B1 | 2/2002 | Cooper | |
| 6,364,888 B1 | 4/2002 | Nieneyer et al. | |
| 6,371,952 B1 | 4/2002 | Madhani et al. | |
| 6,722,842 B1 * | 4/2004 | Sawdon et al. | 414/729 |

FOREIGN PATENT DOCUMENTS

| | | |
|---|---|---|
| EP | 0239409 A1 | 9/1987 |
| EP | 0424687 A1 | 5/1991 |
| EP | 0776738 A2 | 6/1997 |
| EP | 0904741 A1 | 3/1999 |
| WO | WO 91/04711 A1 | 4/1991 |
| WO | WO 92/20295 A1 | 11/1992 |
| WO | WO 93/13916 A1 | 7/1993 |
| WO | WO 94/18881 A1 | 9/1994 |
| WO | WO 94/26167 A1 | 11/1994 |
| WO | WO 97/00649 A1 | 1/1997 |
| WO | WO 97/15240 A1 | 5/1997 |
| WO | WO 98/25666 A1 | 6/1998 |

OTHER PUBLICATIONS

Abstract of a presentation "A Pneumatic Controlled Sewing Device for Endoscopic Application the MIS Sewing Instrument MSI" given at the 3rd World Congress of Endoscopic Surgery in Bordeaux, Jun. 18-20, 1992 (1 page total).

Abstract of a presentation "Concept and Experimental Application of a Surgical Robotic System the Steerable MIS Instrument SMI" given at the 3rd World Congress of Endoscopic Surgery in Bordeaux, Jun. 18-20, 1992 (2 pages total).

Abstract of a presentation given at the 3rd World Congress of Endoscopic Surgery in Bordeaux (Jun. 18-20, 1992), entitled "Session 15/2" (1 page total).

Abstract of a presentation given at the 3rd World Congress of Endoscopic Surgery in Bordeaux (Jun. 18-20, 1992), entitled "Session 15/4" (1 page total).

Abstract of a presentation given at the 3rd World Congress of Endoscopic Surgery in Bordeaux (Jun. 18-20, 1992), entitled "Session 15/5" (1 page total).

Abstract of a presentation given at the 3rd World Congress of Endoscopic Surgery in Bordeaux, Jun. 18-20, 1992, entitled "Session 15/1" (1 page total).

Alexander, III, "A Survey Study of Teleoperators, Robotics, and Remote Systems Technology," Remotely Manned Systems—Exploration and Operation in Space, California Institute of Technology 1973, pp. 449-458.

Alexander, III, "Impacts of Telemation on Modern Society," On the Theory and Practice of Robots and Manipulators vol. II, 1974, pp. 121-136.

Bejczy, "Controlling Remote Manipulators through Kinesthetic Coupling," Computers in Mechanical Engineering 1983, pp. 48-60.

Besant et al., Abstract of a presentation "Camera Control for Laparoscopic Surgery by Speech-Recognizing Robot: Constant Attention and Better Use of Personnel," given at the 3rd World Congress of Endoscopic Surgery in Bordeaux, Jun. 18-20, 1992 (1 page total).

Charles et al., "Design of a Surgeon-Machine Interface for Teleoperated Microsurgery," IEEE 1989 (3 pages total).

Colgate, "Power and Impedance Scaling in Bilateral Manipulation," IEEE, 1991, pp. 2292-2297.

Corcoran, "Robots for the Operating Room," The New York Times, Sunday Jul. 19, 1992, Section 3, p. 9, col. 1 (2 pages total).

Das et al., "Kinematic Control and Visual Display of Redundant Teleoperators," IEEE 1989 pp. 1072-1077.

Dolan et al., "A Robot in an Operating Room: A Bull in a China Shop," IEEE, 1987, pp. 1096-1097.

Gayed et al., "An Advanced Control Micromanipulator for Surgical Applications," Systems Science vol. 13, 1987, pp. 23-34.

Green et al., Abstract of a presentation "Telepresence: Advanced Teleoperator Technology for Minimally Invasive Surgery," given at the 3rd World Congress of Endoscopic Surgery in Bordeaux, Jun. 18-20, 1992 (2 pages total).

Green et al., Abstract of a presentation "Telepresence: Advanced Teleoperator Technology for Minimally Invasive Surgery," given at "Medicine meets virtual reality" symposium in San Diego, Jun. 4-7, 1992 (20 pages total).

Guerrouad et al., "S.M.O.S.: Stereotaxical Microtelemanipulator for Ocular Surgery," IEEE, 1989, pp. 879-880.

Inque et al., "Six-axis Bilateral Control of an Articulated Slave Manipulator Using a Cartesian Master Manipulator," Advanced Robotics, 4, No. 2, 1990, pp. 139-150.

Kazerooni, "Human/Robot Interaction via the Transfer of Power and Information Signals—Part I: Dynamics and Control Analysis," IEEE, 1989, pp. 1632-1640.

Kazerooni, "Human/Robot Interaction via the Transfer of Power and Information Signals—Part II: An Experimental Analysis," IEEE, 1989, pp. 1641-1647.

Krishnan et al., Abstract of a presentation "Design Considerations of a New Generation Endoscope Using Robotics and Computer Vision Technology," given at the 3rd World Congress of Endoscopic Surgery in Bordeaux, Jun. 18-20, 1992 (1 page total).

Lavallee, "A New System for Computer Assisted Neurosurgery," IEEE, 1989, vol. 11, pp. 926-927.

Mair, Industrial Robotics, Prentice Hall, 1988, pp. 41-43, 49-50, 54, 203-209.

(56) References Cited

OTHER PUBLICATIONS

Majima et al., "On a Micro-Manipulator for Medical Application—Stability Consideration of its Bilateral Controller," Mechatronics, 1991, pp. 293-309.
NASA, "Anthropomorphic Remote Manipulator", NASA Tech Briefs, 1991 (1 page total).
Preising et al., "A Literature Review Robots in Medicine," IEEE, Jun. 1991, pp. 13-22 & 71.
Rasor et al., "Endocorporeal Surgery Using Remote Manipulators," Remotely Manned Systems—Exploration and Operation in Space, California Institute of Technology 1973, pp. 483-492.
Sabatini et al., "Force Feedback-Based Telemicromanipulation for Robot Surgery on Soft Tissues," IEEE, 1989, pp. 890-891.
Taubes, "Surgery in Cyberspace," Discover Magazine, Dec. 1994, 85-92.
Taylor et al., "Taming the Bull: Safety in a Precise Surgical Robot," IEEE, 1991, pp. 865-871.
Tejima, "A New Microsurgical Robot System for Corneal Transplantation," Precision Machinery, 1988 vol. 2, pp. 1-9.
Tendick et al., "Analysis of the Surgeon's Grasp for Telerobotic Surgical Manipulation," IEEE, 1989, pp. 914-915.
Thring, "Robots and Telechirs: Manipulator with Memory: Remote Manipulators: Machine Limbs for the Handicapped," Wiley & Sons, 1983.
Transcript of a video presented by SRI at the 3rd World Congress of Endoscopic Surgery in Bordeaux on Jun. 18-20, 1992, in Washington on Apr. 9, 1992, and in San Diego, CA on Jun. 4-7, 1992 entitled "Telepresence Surgery—The Future of Minimally Invasive Medicine" (3 pages total).
Trevelyan et al., "Motion Control for a Sheep Shearing Robot," Proceedings of the 1st International Symposium on Robotics Research, MIT, Cambridge, Massachusetts, USA, 1983, pp. 175.
Vibet, "Properties of Master-Slave Robots," Motor-con, 1987, pp. 309-314.
Wolf et al., "Student Reference Manual for Electronic Instrumentation Laboratories," Prentice Hall, New Jersey 1990, pp. 498 and 499.
Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

* cited by examiner

US 8,641,698 B2

PIVOT POINT ARM FOR ROBOTIC SYSTEM USED TO PERFORM A SURGICAL PROCEDURE

CROSS-REFERENCES TO RELATED APPLICATIONS

This application is a continuation of application Ser. No. 10/411,651, filed Apr. 10, 2003, which is a divisional of application Ser. No. 09/847,736 filed May 1, 2001, now abandoned.

BACKGROUND OF THE INVENTION

1. Field of the Invention

The present invention relates to a pivot arm that can support a surgical instrument during a medical procedure.

2. Background Information

There have been developed surgical robots that assist surgeons in performing medical procedures. By way of example, the assignee of the present invention, Computer Motion, Inc. of Goleta, Calif. sells a medical robotic arm under the trademark AESOP and a medical robotic system under the trademark ZEUS. The AESOP product includes a robotic arm that can be controlled through a foot pedal or voice commands from the surgeon. The AESOP arm is typically used to move an endoscope that is inserted into a patient during a laparoscopic procedure. The ZEUS system includes multiple robotic arms that can control surgical instrument used to perform minimally invasive procedures. The ZEUS robotic arms are controlled by handles that are manipulated by the surgeon.

Coronary artery bypass graft (CABG) procedures can be performed minimally invasively using the ZEUS and AESOP products. The surgical instruments and endoscope are inserted through small incisions created in the chest of the patient. The robotic arms include both active and passive joints that move the instruments and endoscope about corresponding pivot points. The pivot points are created by the incisions formed in the patient.

Some surgeons are uncomfortable performing minimally invasive CABG procedures and will only perform the procedure with an opened chest cavity. There may still be a desire to utilize robotic arms to control the instruments even during an open chest procedure. For example, the ZEUS system will filter the natural hand tremor of the surgeon.

There are no incisions or corresponding pivot points in an open chest procedure. Unfortunately, the ZEUS and AESOP systems will not function properly without the pivot points created by the incisions. It is therefore desirable to create a pivot point for the robotic arms to function during a non-minimally invasive procedure.

Computer motion has provided a support arm that could support an instrument during a non-minimally invasive procedure. The instrument could be inserted through a diaphragm located at the distal end of the arm. The diaphragm provided some flexibility to pivot the instrument but not enough to allow sufficient movement by a robotic arm to perform most medical procedures.

BRIEF SUMMARY OF THE INVENTION

One embodiment of the present invention includes a pivot port that has an adapter coupled to a pivot arm by a joint. Another embodiment includes a ball joint that is coupled to a pivot arm.

DETAILED DESCRIPTION OF THE PREFERRED EMBODIMENT

In general the present invention includes a pivot port that can provide a pivot point for a surgical instrument moved by a robotic arm. The pivot port may be held in a stationary position by a support arm assembly that is attached to a table. The pivot port may include either an adapter or a ball joint that can support the surgical instrument. The pivot port allows the instrument to pivot relative to a patient. The pivot arm allows the robotically controlled surgical instrument to be used in a non-minimally invasive procedure such as an open chest coronary artery bypass graft (CABG) procedure. Although use of the pivot arm in open chest CABG procedures is described, it is to be understood that the pivot arm can be used in other surgical procedures including minimally invasive procedures. For example, the pivot arm can be used to hold an instrument for a minimally invasive CABG procedure. Additionally, the pivot arm can hold instruments that are not robotically controlled.

Figure 1:
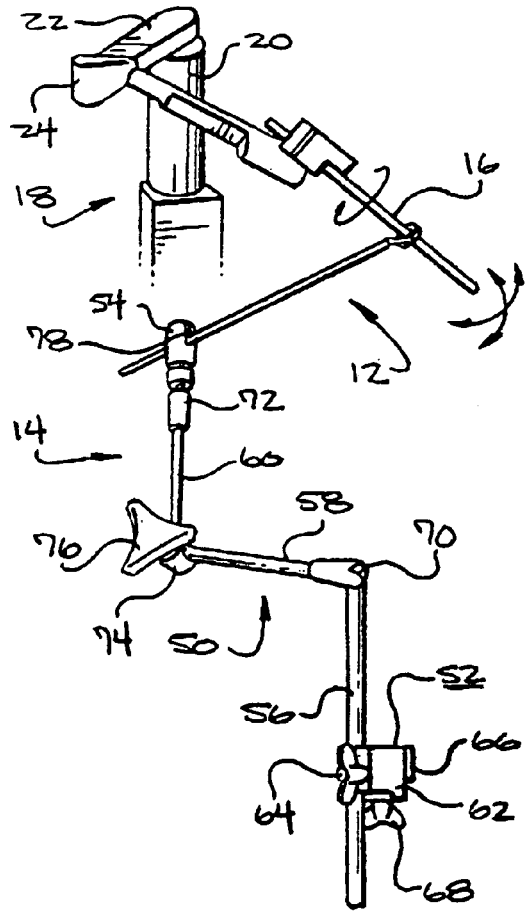
FIG. 1 is an illustration of an embodiment of a medical system of the present invention.

Referring to the drawings more particularly by reference numbers, FIG. 1 shows an embodiment of a medical system 10 of the present invention. The system 10 may include a pivot port 12 that is held in a stationary position by a support arm assembly 14. The support arm assembly 14 may be attached to a surgical table (not shown).

A surgical instrument 16 can be coupled to the pivot port 12. The surgical instrument 16 can be coupled to a robotic arm 18. The pivot port 12 is constructed so that the instrument 16 can pivot relative to the arm 12 with a sufficient range of motion so that medical procedures can be performed with the robotic arm 18.

The robotic arm 18 may include a linear actuator 20, a first rotary actuator 22 and a second rotary actuator 24 that are controlled by a computer (not shown) to move the surgical instrument 16. The robotic arm 18 may also have an end effector (not shown) to spin and/or actuate the instrument 16. The arm 18 may also have passive joints (not shown) that allow the instrument 16 to pivot about the pivot port 12. The robotic arm 18 may be a product sold by Computer Motion, Inc. of Goleta, Calif. under the trademark AESOP or a Computer Motion product sold under the trademark ZEUS, which are hereby incorporated by reference.

Figure 2:
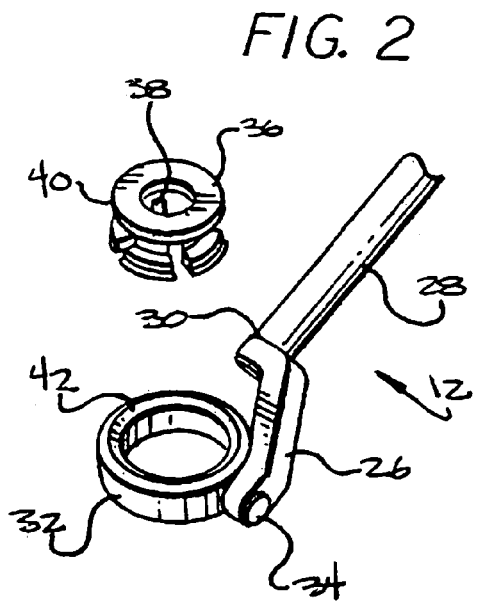
FIG. 2 is a perspective view of a pivot port of the medical system.

FIG. 2 shows an embodiment of the pivot port 12. The pivot port 12 includes a first link 26 that is configured as a single connecting piece having pivotal ends, wherein a proximal end of the first link 26 is bent at an approximately 45 degree angle relative to a middle segment of the first link 26 and a distal end of the first link 26 is bent at an approximately 135 degree angle relative to the middle segment of the first link 26. The proximal end of the first link 26 is directly connected to a pivot arm 28 by a first joint 30 that defines a first axis of rotation which is approximately coincident with a longitudinal axis of the pivot arm 28. The distal end of the first link 26 is directly connected to only one outer side of a ring 32 by a second joint 34 that defines a second axis of rotation which is approximately orthogonal to the first axis of rotation and which is approximately coincident with a diameter of the ring 32.

The pivot port 12 may include an adapter 36 that can be coupled to the ring 32. The surgical instrument 16 can extend through an aperture 38 of the adapter 36. The aperture 38 should have a diameter that allows the instrument 16 to spin and translate relative to the pivot port 12. The first 30 and second 34 joints allow the ring 32 and corresponding instrument to pivot about the arm 28 to provide yaw and pitch rotation.

The adapter 36 may have an outer annular flange 40 that rests on an inner annular lip 42 of the ring 32. The adapter 36 may be constructed to be readily attached and detached from the ring 32. This allows adapters having different aperture diameters to be inserted into the pivot port 10 to accommodate different instrument sizes.

Figure 3:
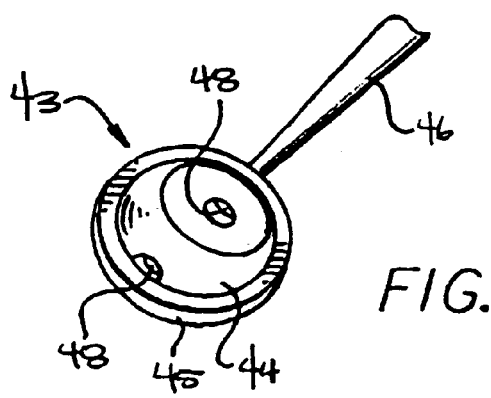
FIG. 3 is a perspective view of an alternate embodiment of the pivot port.

FIG. 3 shows an alternate embodiment of a pivot port 43 that includes a ball joint 44 that can pivot relative to a ring 45. The ring 45 is attached to a pivot arm 46. The ball joint 44 may have a plurality of apertures 48 that can receive a surgical instrument 16. The ball joint 42 allows the instrument 16 to pivot relative to the arm 46. Opposing pairs of apertures 48 can be constructed to have different diameters to receive instruments of different sizes. The ball joint 44 thus provides a joint that can accommodate different instrument sizes without having to replace the joint as may be required in the embodiment shown in FIG. 2.

Referring again to FIG. 1, support arm assembly 14 includes a support arm 50 that is coupled to a table mount 52. The table mount 52 is adapted to be secured to a surgical table (not shown). The support arm assembly 14 further includes an end effector 54 that is coupled to the arm 50. The end effector 54 is adapted to hold the pivot arm 28 or 46 of the pivot port 12, or 43, respectively.

The arm 50 may include a first linkage 56 that is coupled to the table mount 52 and a second linkage 58 coupled to the first linkage 56. The arm 50 may further have a third linkage 60 coupled to the second linkage 58.

The first linkage 56 may extend through a clearance hole (not shown) in a base 62 of the table mount 52. The table mount 52 may have an arm clamp 64 that can be rotated to engage the first linkage 56 and secure the position of the end effector 54 in a vertical direction. The arm clamp 64 can be rotated in an opposite direction to disengage the clamp 64 and allow an end user to move the first linkage 56 and adjust the height of the end effector 54 and pivot port.

The table mount base 24 may include a jaw section 66 that can clasp onto the rail of an operating table (not shown). The jaw section 66 can be secured to the table rail by a table clamp 68.

The second linkage 58 may be coupled to the first linkage 56 by a first ball joint 70. Likewise, the end effector 54 may be coupled to the third linkage 60 by a second ball joint 72. The third linkage 60 may be coupled to the second linkage 20 by a pivot joint 74. The ball joints 70 and 72, and pivot joint 74 provide the support arm six degrees of freedom. The position of the arm 50 and end effector 54 can be secured and locked in place by rotating a locking knob 76. The locking knob 76 clamps the pivot joint 74 to prevent relative movement between the third 60 and second 58 linkages. Rotation of the locking knob 76 also moves corresponding wedges (not shown) into the ball joints 70 and 72 to secure and lock the second linkage 58 and the end effector 54, respectively. The arm 50 and table mount 52 can be purchased from KARL STORZ under part number 28172H. The end effector 54 may have a spring biased retractable jaw 78 that can capture the pivot port 12. The retractable jaw 78 allows an operator to readily attach and detach the pivot port 12 to the support arm assembly 14. The joints 70, 72 and 74 allow the operator to adjust the pivot port 12 location and the instrument 16.

The following medical procedure can be performed with the pivot point 12 of the present invention. A patient's chest cavity may be opened and the pivot port 12 may be attached to the support arm assembly 14 adjacent to the open chest cavity. A surgical instrument 16 may then be inserted through the pivot port 12 and attached to the robotic arm 18. The robotic arm 18 may then be actuated to move the instrument 16 and perform a procedure. The pivot port 12 allows the instrument to pivot about the port 12. When the procedure is completed, the instrument 16 may be decoupled from the robotic arm 18 and pulled out of the pivot port 12. The pivot port 12 may then be detached from the support arm assembly 14.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art. For example, although an open chest procedure is described, the pivot port can provide a pivot point for any type of medical procedure.

What is claimed is:

1. A pivot port that can support a surgical instrument controlled by a robotic arm, comprising:
   a pivot arm;
   a ring having an inner annular ring lip;
   a first link configured as a single connecting piece having pivotal ends;
   an adapter that has an aperture and an outer annular flange, wherein the aperture is adapted to receive the surgical instrument, and wherein the outer annular flange rests on the inner annular ring lip of the ring so that the ring supports the adapter; and,
   first and second joints, wherein a proximal end of the first link is directly connected to the pivot arm by the first joint so that the proximal end of the first link is constrained to only be rotatable at the first joint about a first axis of rotation that is parallel with a longitudinal axis of the pivot arm and a distal end of the first link is directly connected to only one outer side of the ring by the second joint so that the ring and the adapter are rotatable at the second joint about a second axis of rotation that is maintained by a shape of the first link to be approximately orthogonal to the first axis of rotation so as to allow the surgical instrument to pivot about said aperture when the pivot arm is locked in place and the instrument is received in the aperture.

2. The pivot port of claim 1, wherein the first axis of rotation is coincident with the longitudinal axis of the pivot arm.

3. The pivot port of claim 1, wherein the second axis of rotation is coincident with the diameter of the ring.

4. The pivot port of claim 1, wherein the first link is freely rotatable at the first joint and the adapter is freely rotatable at the second joint while the surgical instrument is being controlled by the robotic arm.

5. The pivot port of claim 1, wherein the adapter is constrained to only be rotatable at the second joint about the second axis of rotation.

6. The pivot port of claim 1, wherein the first and second axes of rotation intersect within the aperture of the adapter so that the intersection serves as a pivot point for the surgical instrument.

7. The pivot port of claim 1, wherein the proximal end of the first link is bent at an approximately 45 degree angle relative to a middle segment of the first link and the distal end of the first link is bent at an approximately 135 degree angle relative to the middle segment of the first link.

* * * * *